US009110036B2

(12) United States Patent
Lepage

(10) Patent No.: US 9,110,036 B2
(45) Date of Patent: Aug. 18, 2015

(54) ASSEMBLY WITH A UNIVERSAL MANIPULATOR FOR INSPECTING DOVETAIL OF DIFFERENT SIZES

(71) Applicant: Benoit Lepage, Ancienne-Lorette (CA)

(72) Inventor: Benoit Lepage, Ancienne-Lorette (CA)

(73) Assignee: OLYMPUS NDT, INC., Waltham, MA (US)

(*) Notice: Subject to any disclaimer, the term of this patent is extended or adjusted under 35 U.S.C. 154(b) by 163 days.

(21) Appl. No.: 13/955,078

(22) Filed: Jul. 31, 2013

(65) Prior Publication Data

US 2014/0035568 A1 Feb. 6, 2014

Related U.S. Application Data

(60) Provisional application No. 61/678,857, filed on Aug. 2, 2012.

(51) Int. Cl.
*G01N 27/82* (2006.01)
*G01N 27/90* (2006.01)

(52) U.S. Cl.
CPC ............ *G01N 27/904* (2013.01); *G01N 27/902* (2013.01)

(58) Field of Classification Search
CPC .......................... G01N 27/902; G01N 27/904
See application file for complete search history.

(56) References Cited

U.S. PATENT DOCUMENTS

| 5,315,234 | A | * | 5/1994 | Sutton et al. | 324/242 |
|---|---|---|---|---|---|
| 5,834,937 | A | * | 11/1998 | Burris | 324/219 |
| 6,479,989 | B2 | * | 11/2002 | Taylor | 324/219 |
| 6,545,467 | B1 | * | 4/2003 | Batzinger et al. | 324/219 |
| 6,608,478 | B1 | * | 8/2003 | Dziech et al. | 324/262 |
| 7,800,364 | B2 | * | 9/2010 | Briffa et al. | 324/240 |
| 2013/0199279 | A1 | * | 8/2013 | Boles et al. | 73/112.01 |

* cited by examiner

*Primary Examiner* — Patrick Assouad
*Assistant Examiner* — Demetrius Pretlow
(74) *Attorney, Agent, or Firm* — C. Tricia Liu

(57) ABSTRACT

Disclosed is an ECA probes assembly capable of providing reliable and durable ECA inspections of dovetail slots without the use of an external guiding mechanism. The design combines a novel universal probe manipulator with a probe support suited for a wide range of probe supports which fit a rage of turbine disks. The probe support embodies a rigid yet expandable core, exerting a force pushing the array probe against the inner cavity of the dovetails. The pushing force is strategically located in critical areas of the dovetail leading to array probe to be self-guiding into the dovetail, and to provide optimum performance with consistent and stable lift-off.

16 Claims, 7 Drawing Sheets

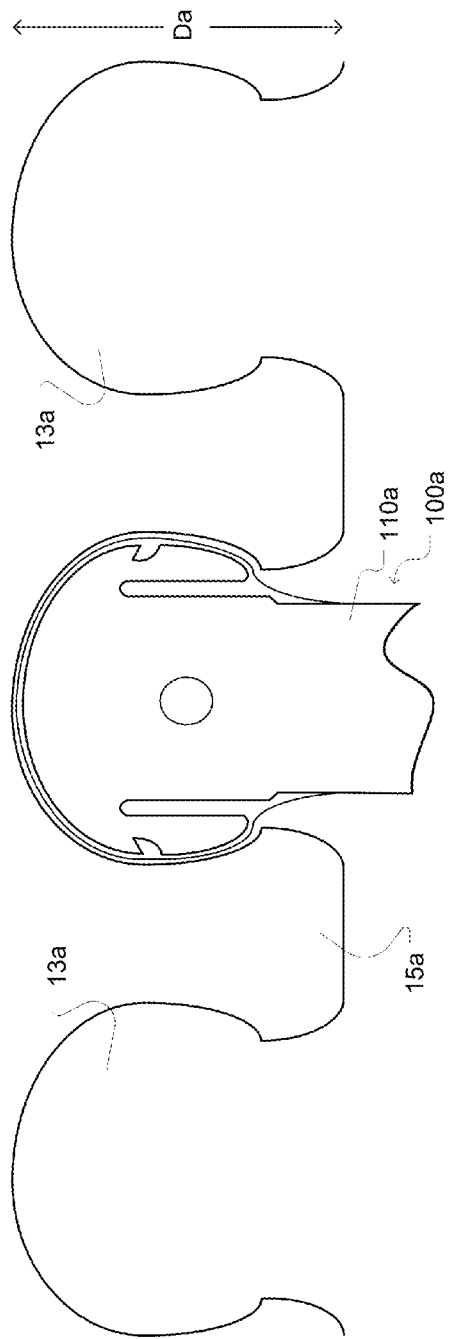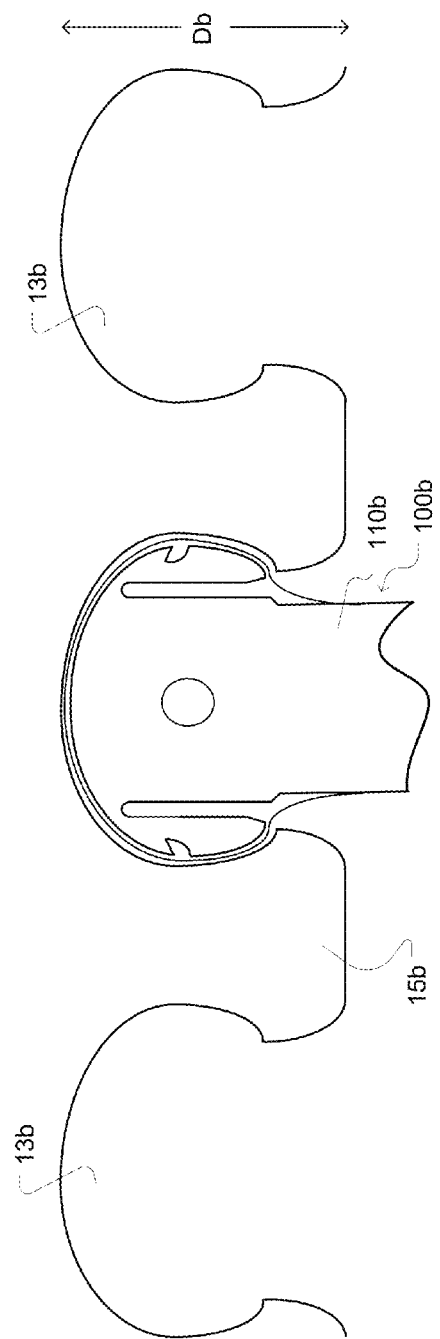

ASSEMBLY WITH A UNIVERSAL MANIPULATOR FOR INSPECTING DOVETAIL OF DIFFERENT SIZES

CROSS-REFERENCE TO RELATED APPLICATIONS

This application claims the benefit and priority of U.S. Provisional patent application Ser. No. 61678857 filed Aug. 2, 2012 entitled AN NDT ASSEMBLY WITH A UNIVERSAL MANIPULATOR FOR INSPECTING DOVETAIL OF DIFFERENT SIZES, the entire disclosure of which is incorporated herein by reference.

FIELD OF THE INVENTION

The present invention relates to an assembly used for a non-destructive inspection or testing (NDI/NDT) device, particularly it relates to an assembly for inspecting dovetail slots in turbo machine rotor disk by using eddy current array probes.

BACKGROUND OF THE INVENTION

Eddy current array (ECA) inspection is commonly used to detect flaws in surfaces of manufactured metal components such as turbine engine components. During this type of inspection, electro-magnetic induction is used to induce eddy currents in the component being inspected. A plurality of sensors inside an ECA probe separately generates alternating magnetic fields, which induces the eddy currents in the component while the probe is moved near the component. When flaws are present in the component, the flow of eddy currents is altered. The altered eddy currents produces changes in a secondary magnetic field which are detected by the array of sensors inside the ECA probe. An ECA acquisition unit monitors variations of secondary magnetic fields to produce readings for each of the ECA probe sensors which are typically representative of the flaw size. A complete scan of the dovetail is typically achieved by moving the probe along the entire dovetail length while acquiring ECA readings and position information in order to construct a cscan image representative of the actual condition of whole inspected surface of the dovetail.

The reliability and accuracy of the measurement depend on the ECA probe being properly positioned in the dovetail in order to maintain, for all inspections, a relatively constant sensor to part distance (Lift-off). Another important aspect is the ability to track the position of the probe in the dovetail slot in order to accurately reconstruct the cscan image.

Past solutions to produce a reliable cscan image from an ECA scan of a dovetail slot were not adapted for the deployment of a versatile, portable and reliable product. For example, U.S. Pat. No. 7,800,364 describes a solution where the probe manipulator itself provides a precise position reference to the probe using the adjacent dovetail slots as reference. Such a solution requires an important redesign for every dovetail design and in thus not adapted for a product with large deployment.

Other solutions provided patents such as U.S. Pat. Nos. 5,315,234, 5,442,286, 6,339,326, 6,545,467, 6,563,307 and 6,812,697 use conformable probe supports and some actuation mechanism to expand the probes and force the sensors onto the dovetail inner surfaces. In this case, one drawback is the frequent probe damage that occurs when the ECA probe moves near part edges which causes excessive strain on the probe. Another drawback is the need for automation in order to expand the probes in the dovetail slot, which typically requires the use of a robot to conduct the inspection.

Therefore there is an unmet need for a solution to provide a portable and reliable ECA probe and manipulator system easily adaptable to multiple turbine disk designs.

SUMMARY OF THE INVENTION

The present disclosure provides a method and design of a novel ECA probes assembly capable of providing reliable and durable ECA inspections of dovetail slots without the use of an external guiding mechanism.

The design combines a novel universal probe manipulator with a probe support suited for a wide range of probe supports which fit a rage of turbine disks. The probe support embodies a rigid yet expandable core, exerting a force pushing the array probe against the inner cavity of the dovetails. The pushing force is strategically located in critical areas of the dovetail leading to the array probe to be self-guiding into the dovetail, and to provide optimum performance with consistent and stable lift-off through the entire surface of the dovetail.

Advantages of the invention include the use of the same probe manipulator for a wide range of probe supports fitting rages of turbine disk designs.

Advantages of the invention also include the use of probe support perfectly optimally suited for the usage of a flexible printed circuit ECA probe for dovetail inspections without the drawback of existing solutions, i.e., durability problems, the required use of a robot to conduct the scans, etc.

In addition, advantages of the invention also include the significantly improved performance in the areas close to dovetail edges by providing a more stable and snuggly fit between the probe and the cavity surface in these critical areas.

BRIEF DESCRIPTION OF THE DRAWINGS

FIG. 7a is a cross-sectional view of a first ECA probe and probe support in which the probe support fits into a first set of dovetail slots.

FIG. 7b is a cross-sectional view of a second ECA probe and probe support in which the probe support fits into a second set of dovetail slots.

DETAILED DESCRIPTION OF THE INVENTION

Figure 1:
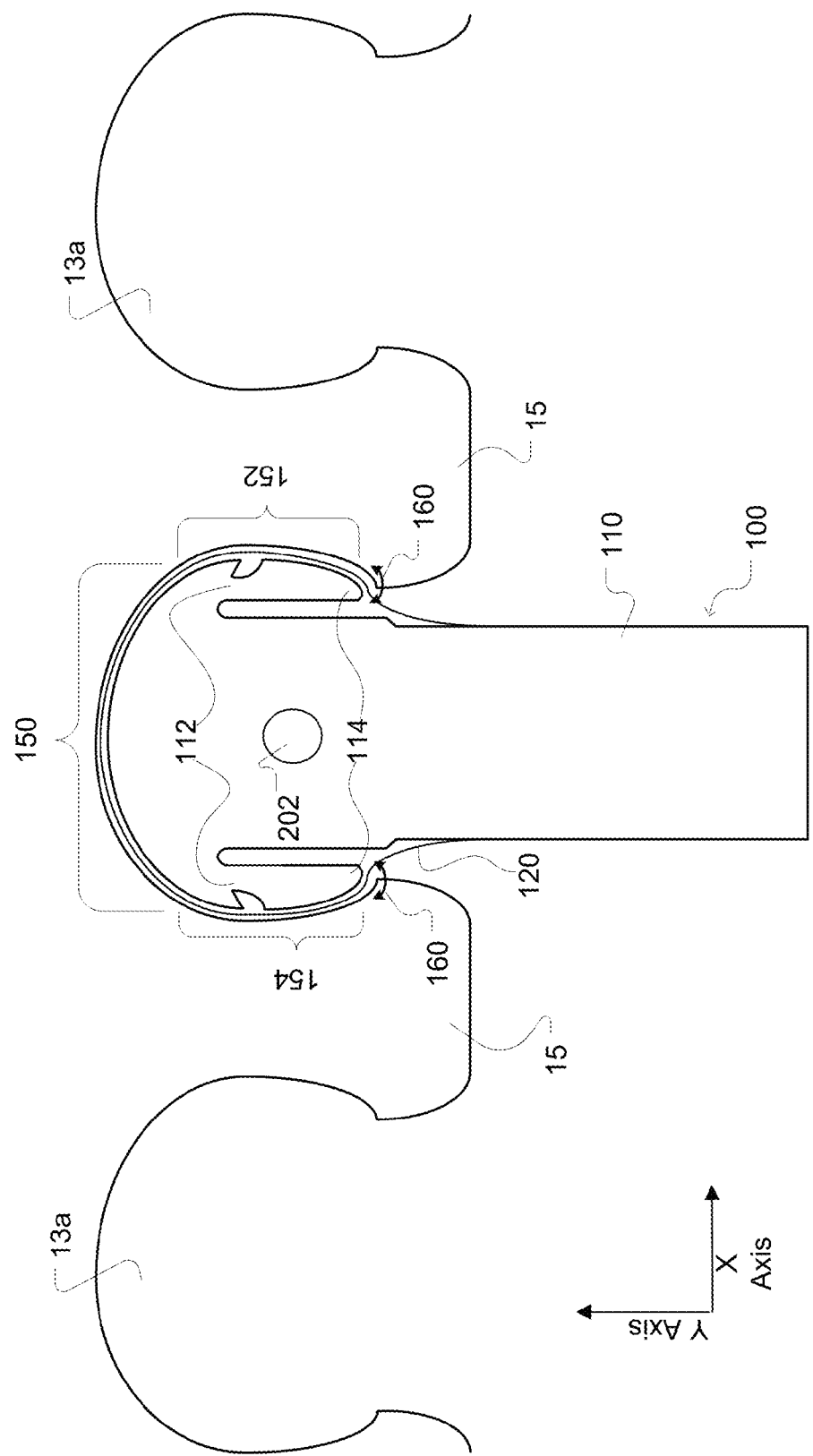
FIG. 1 is a cross-sectional view of the ECA probe and probe support illustrating how the probe support of the invention can fit into the inspected dovetail slot to provide self-guiding properties centering and pushing the probe against the inner surface of the dovetail slot.
Figure 2:
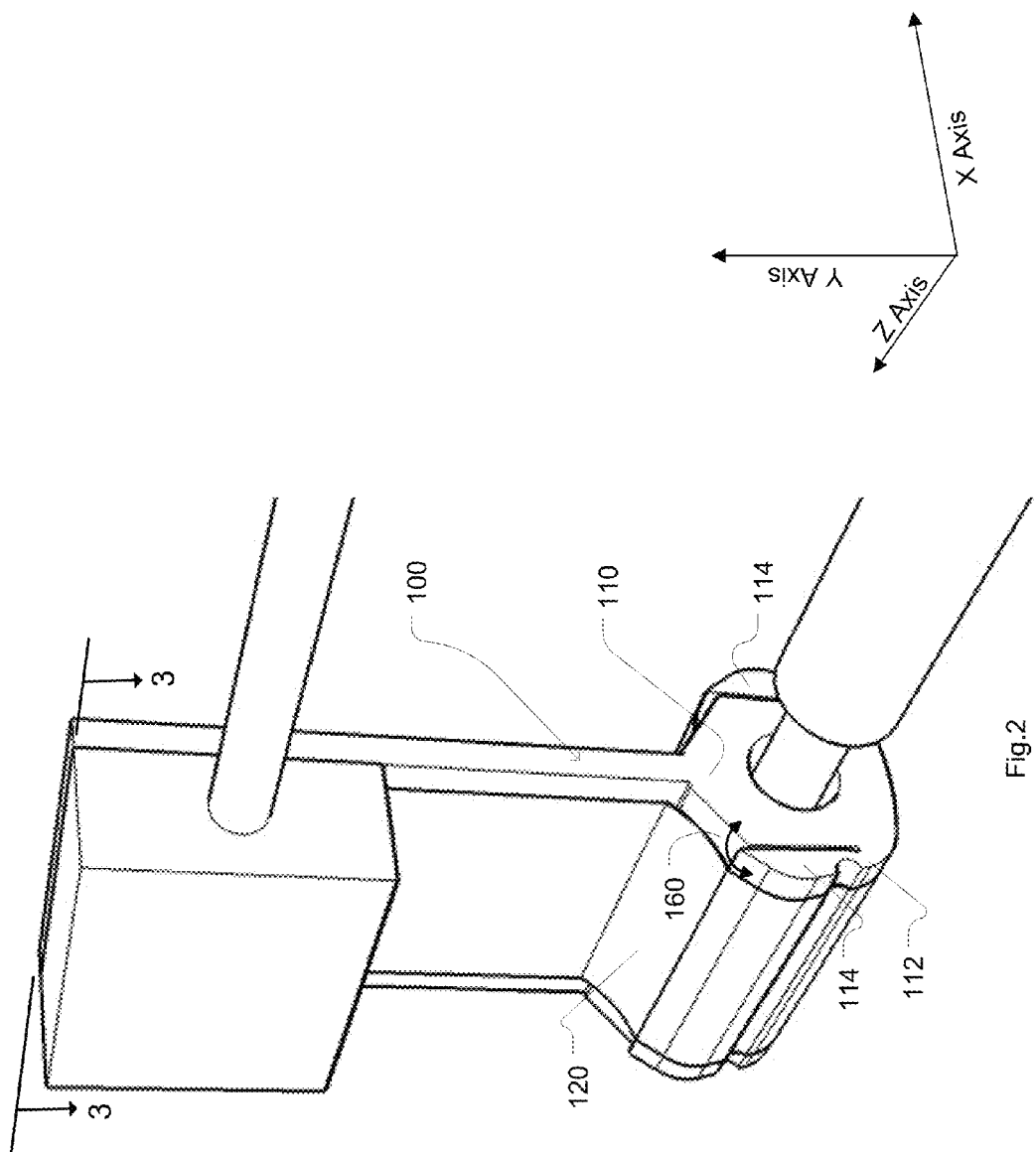
FIG. 2 is a perspective view of the self-guiding probe assembly of the invention.

Referring to FIGS. 1 and 2, a first aspect of the invention is the self guiding properties of a ECA probe assembly 100. By opposition to the prior art probe of U.S. Pat. No. 7,800,364 which relies on the manipulator itself for precisely guiding the plurality of sensors of the ECA probe in a dovetail 13 of a rotor disk 15, new probe assembly 100 of the invention uses the profile of dovetail 13 for precisely maintaining the lift-off distance within some defined limits.

For probe assembly 100 of the preferred embodiment (illustrated on FIG. 1 in contact with dovetail 13 and in FIG. 2, perspective view, not in contact with dovetail 13 and in a downward motion 4), lift-off is controlled by pushing a thin ECA probe 120, which preferably comprises groups of sensors, with each group consisting of any number of individual sensors and is preferably manufactured using a form of mat or sheet with flexible backing, such as flexible printed circuit board technologies, being attached (either permanently or using re-attachable means) to a probe support 110, which is made out of rigid but flexible material (such as ABS, PEEK, Delrin, etc.). In order to make probe 120 re-attachable, an adhesive material can be applied between probe 120 and probe support 110. ECA probe 120 is attached to probe support 110 in such a way that ECA probe 120 does not experience movement relative to probe support 110. In this way the locations of each of the plurality of sensors in the cross section of probe assembly 100 can be known to an encoder system 354 (not shown, refer to FIG. 5). Because of the shape of dovetail 13, probe support 110 is correspondingly Ω-shaped to be able to fit into and out of dovetail 13. Probe support 110's flexibility is exploited by forming pivot points 112 at some strategic locations. Manufacturing probe support 110 to leave a relatively thin layer of material at pivot points 112, where the probe support 110 is meant to bend, forms a naturally spring loaded shape 114, which forces contact between ECA probe 120 and dovetail slot 13 at all inspected areas 150, 152, 154 (Shown in FIG. 1, not shown in FIG. 2). Shown also in FIG. 1 is a ball bearing assembly 202 as part of probe support 110, which will be explained in FIG. 3

Probe support 110's rigidity and pre-defined pivot point 112 make it possible to control spring loaded shape 114's movement 160 in order to obtain the same pressure and movement on both sides of ECA probe 120. Another unique aspect of the invention is to provide almost uniform movement 160 along the whole length of ECA probe 120, even if ECA probe 120 is not completely inserted in the dovetail. This property is important to obtain better inspection performances near the part edges compared to prior art solutions, such as U.S. Pat. Nos. 5,315,234, 5,442,286, 6,339,326, 6,545,467, 6,563,307 and 6,812,697, and to provide longer probe life by eliminating most of the strains in the probe itself caused by the use of a soft compressed body to provide the probe pressure on the inspected component.

The location of pivot points 112 is determined by considering the mechanical tolerances of dovetail 13 (which are typically of the order of +/−0.05 mm) and the positions of the inspected areas in dovetail 13, in order to minimize the possible lift-off variations between ECA probe 120's elements and the inspected surface. Probe 120's thickness (typically about 0.15 mm) and preferably some protective low friction tape (typically 0.07 5mm thick Teflon) is also considered when probe support 110 is designed. Therefore, even if dovetail 13's shape is not perfectly constant from other dovetails, the inspected surface can be used to guide probe 120 during the inspection.

Figure 3:
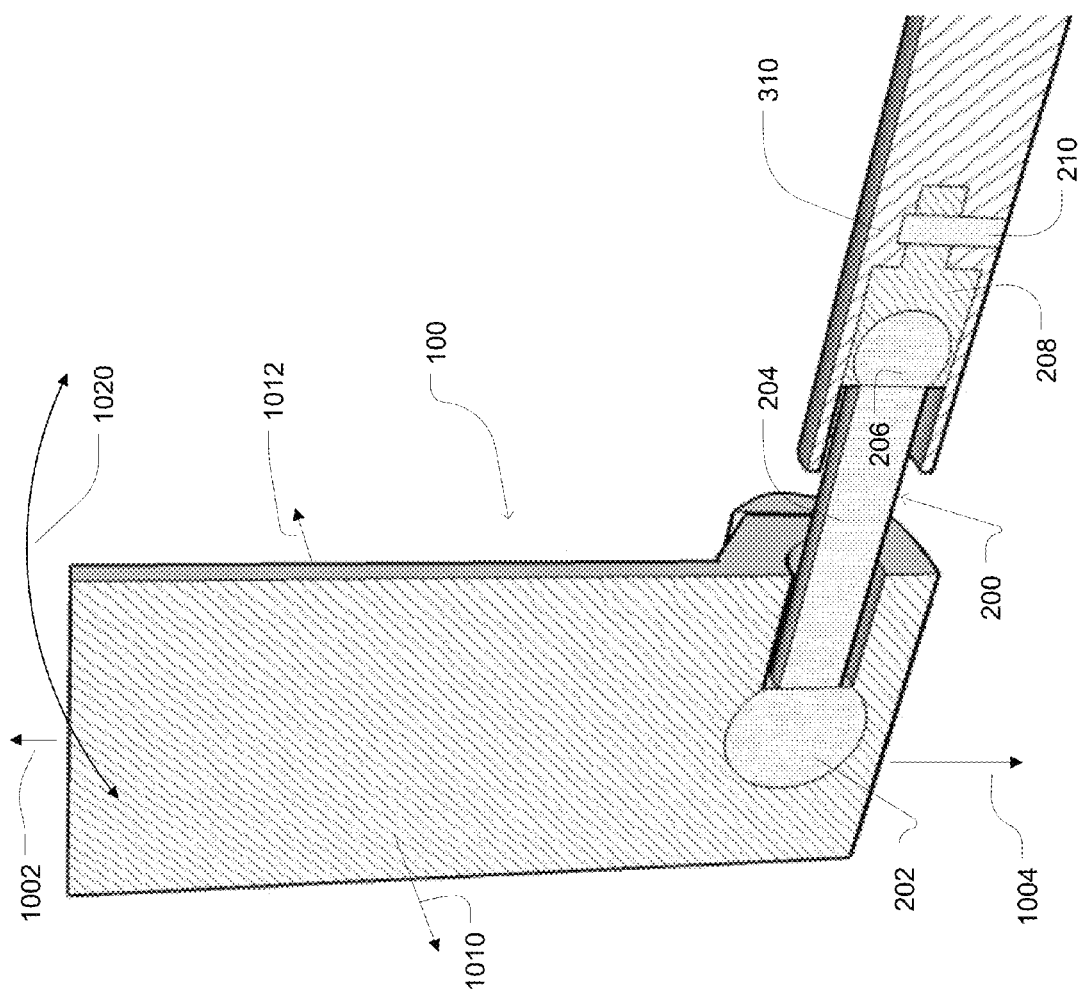
FIG. 3 is a cross sectional view of the self-guiding probe assembly of the invention.

Referring now to FIG. 3, which is a cross section of FIG. 2, shows how probe assembly 100 can be attached to a manipulator arm 310 in order to take full benefit of the self guiding properties of probe assembly 100. Probe assembly 100 is connected to manipulator arm 310 using a link system 200, allowing independent movement of the probe assembly 100 in an up direction 1002, a down direction 1004, a right direction 1012, a left direction 1010 and an angular direction 1020. Link system 200 comprises a central portion 204, which interconnects two ball joint assemblies 202 and 206 (or equivalent mechanical system). Ball joint assembly 206 is preferably integrated into a small detachable coupling component 208 which makes it possible for the user to easily separate probe assembly 100 from manipulator arm 310. For example, the connection between probe assembly 100 and manipulator arm 310 can be achieved using a set screw 210.

Typically, ball joint assembly 202's position in probe support 110 on the X, Y plane is in the center of the areas defined by 150, 152 and 154 (not shown, refer to FIG. 1). Typically, ball joint assembly 202's position in the probe support 110 on the Z Axis is located in the center of the probe support 110. Ball joint assembly 202 is preferably located here in order to avoid inducing torque in probe assembly 100 when it is pushed in or pulled out of dovetail 13 (not shown, refer to FIG. 1).

Figure 4:
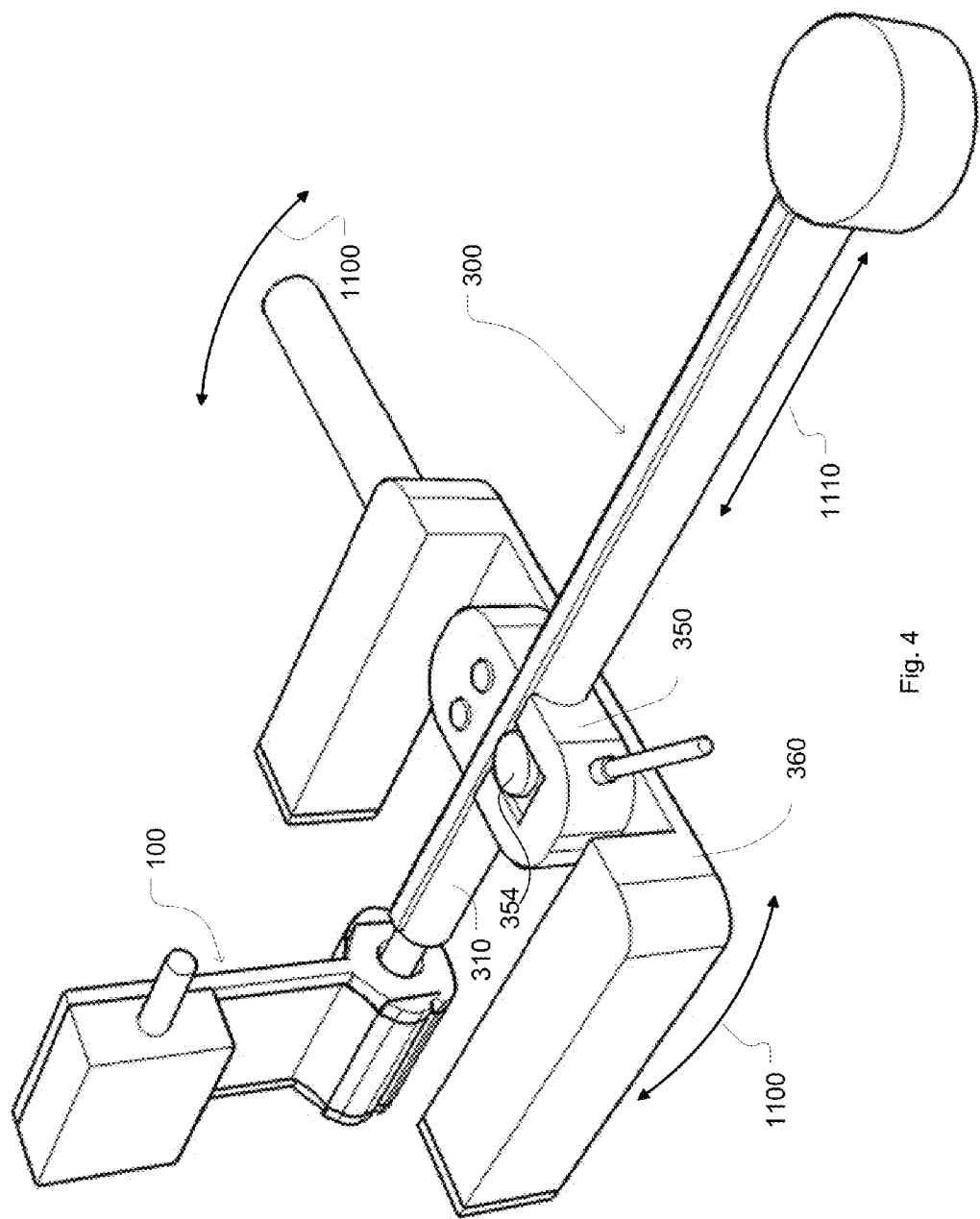
FIG. 4 is an isometric view of the universal probe assembly, providing elaboration on the manipulator.

Now looking at FIG. 4, a universal probe manipulator 300 is shown with probe assembly 100 attached. Manipulator 300 includes a center portion 350, a swivel base 360 and arm 310. Center portion 350 and base 360 are attached in order to allow a rotational degree of freedom 1100. Center portion 350 and arm 310 are also attached in order to allow a translation degree of freedom 1110.

Figure 5:
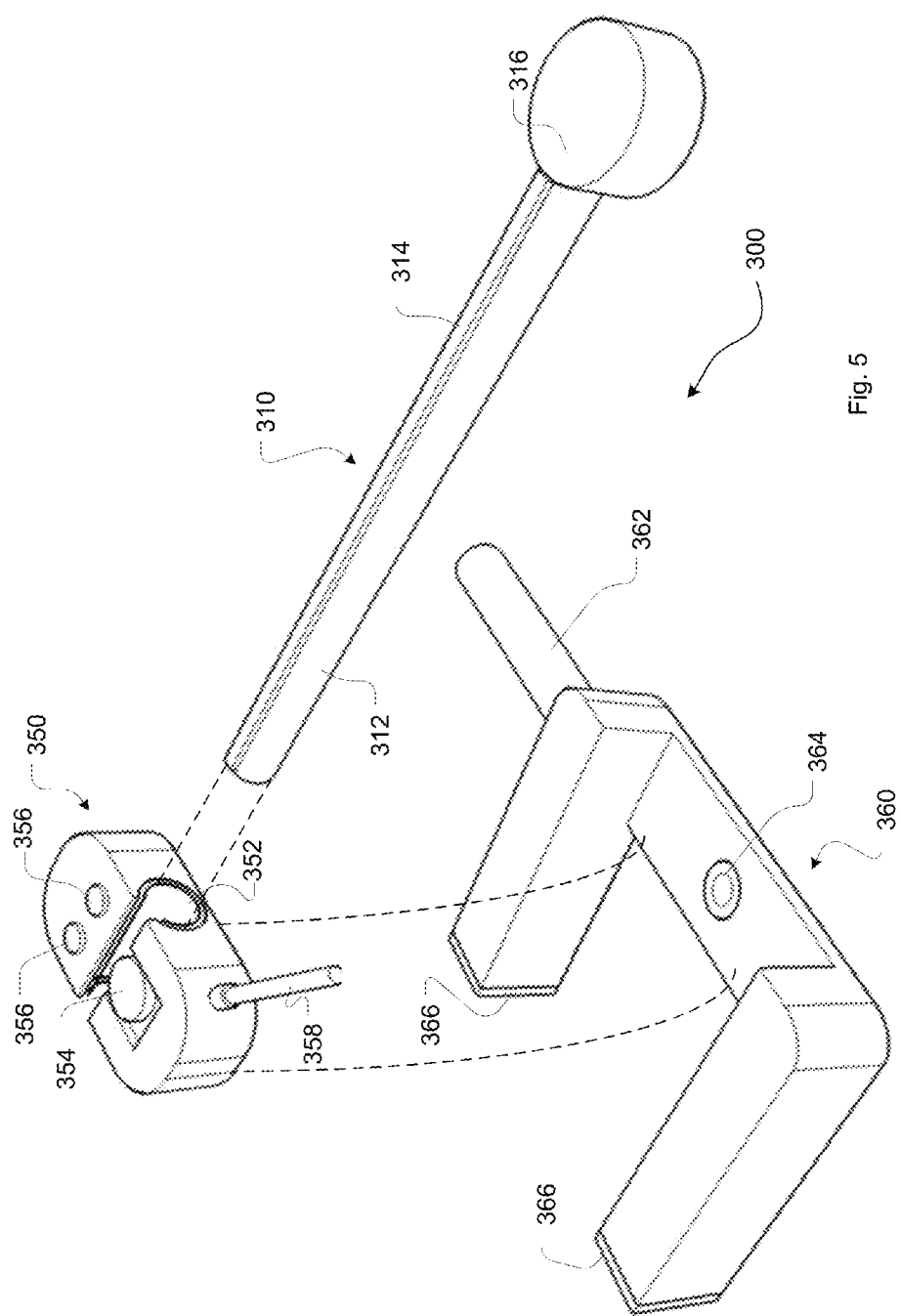
FIG. 5 is an exploded view of the various components of the universal manipulator.

FIG. 5 provides an exploded view on the sub-components of manipulator 300. Arm 310 comprises a rectilinear rack 314, a shaft 312 and a handle 316. Center portion 350 comprises encoder system 354 to connect with rectilinear rack 314, a linear bearing 352 to provide translational degree of freedom 1110 (not shown, refer to FIG. 4), buttons 356 to remotely operate the acquisition system with common operations (such as start/stop and save data) and a scanner interface cable 358. Swivel base 360 comprises a handle 362, a pivot system 364, which allows rotational degree of freedom 1100 (not shown, refer to FIG. 4), and contact shoes 366. Linear bearing 352 is affixed to swivel base 360 via pivot system 364 so that, when swivel base 360 is pushed snuggly against a disk face 502 (shown in FIG. 6), a predetermined degree of freedom of movement is allowed between shaft 312 and swivel base 360 in a plane that is parallel to the axial direction and perpendicular to disk face 502.

Figure 6:
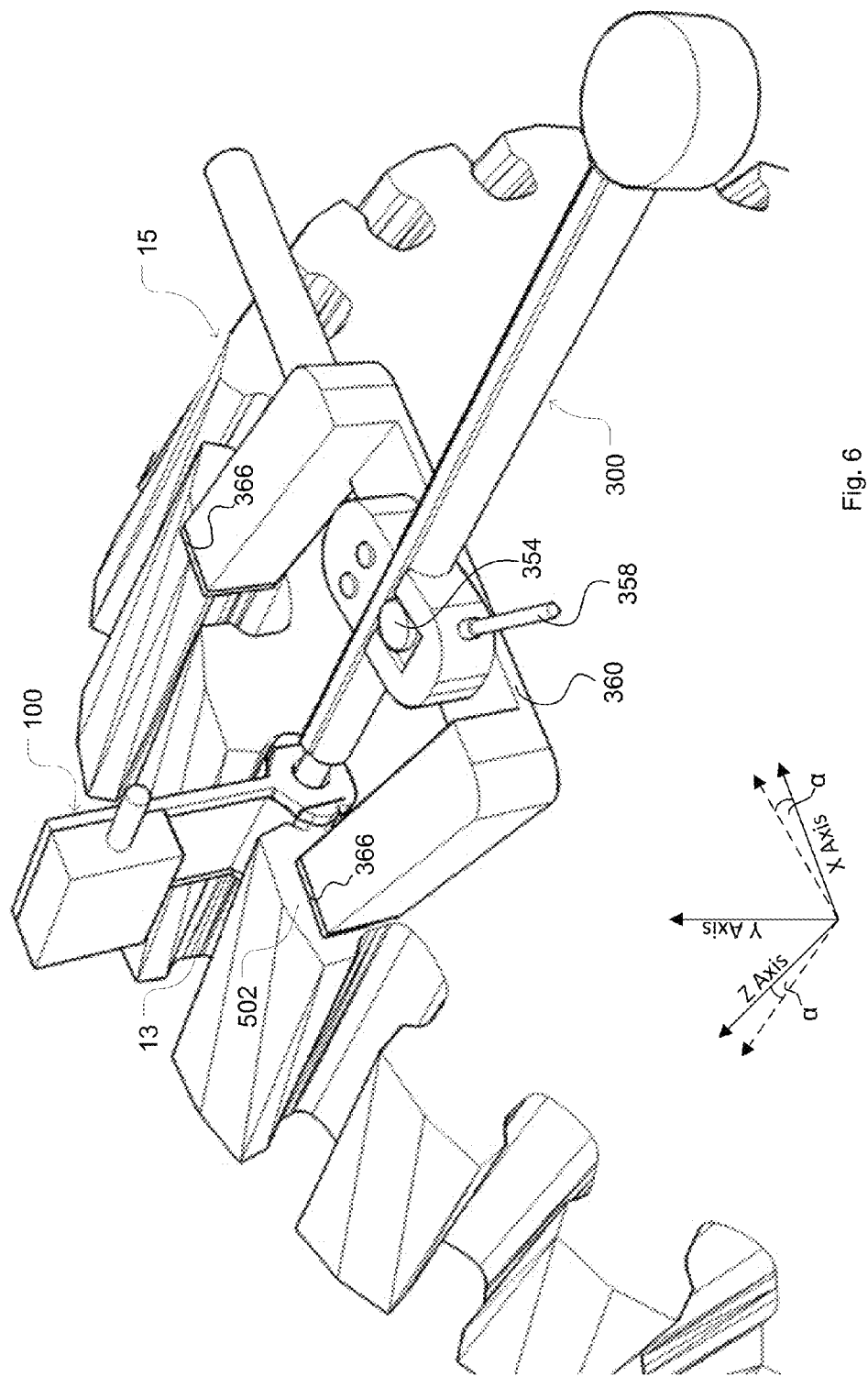
FIG. 6 is a perspective view illustrating the universal dovetail probe manipulator attached on a turbine disk.

Now looking at FIG. 6, which illustrates manipulator, 300 and probe assembly 100 during the inspection of dovetail slot 13. Both contact shoes 366 are in contact with disk face 502 during the inspection. This contact between contact shoes 366 and disk face 502 is possible due to the rotational degree of freedom 1100 (not shown, refer to FIG. 4). Contact shoes 366 are typically made out of rubber or similar material in order to provide a smooth and stable contact with disk face 502. Contact shoes 366 are also wide enough to contact to disk face 502 with various disk designs with different dovetail shapes and sizes. Base 360 is U shaped in order to completely retract probe 120 from dovetail 13 during the inspection so that dovetail 13 can be scanned completely in one scan while contact shoes 366 are sitting on disk face 502. The width of the U shape for base 360 is large enough to allow the required rotational degree of freedom 1100 (not shown, refer to FIG. 4) to cover Z Axis dovetail angle a found on most turbine disk design.

Dovetail 13 can be fully inspected in one scan either by scanning while pushing probe assembly 100 in dovetail 13 or by scanning while pulling probe assembly 100 out of dovetail 13 using translation movement 1110 (not shown, refer to FIG. 4), this position in the Z axis is recorded by encoder system 354 and transmitted to the ECA acquisition unit (not shown) through cable 358. A mapping of the information recorded using ECA probe assembly 100 along dovetail 13 length can then by displayed by the acquisition unit (not shown). Inspection of dovetail 13 by pulling the probe is typically preferred as the action of pulling the probe naturally forces shoes 366 in contact with disk face 502.

While Prior art solution (such as U.S. Pat. No. 7,800,364) did require a specific probe and manipulator design for each turbine disk design, the combined use of self-guiding probe assembly 100 and manipulator 300 with rotational degree of freedom 1100 and contact shoes 366 to sit on disk face 502 makes it possible to use the same probe manipulator 300 for a wide range of turbine disk designs. As for the probe, it is typically required to redesign only the probe support 110 in order to adapt to a dovetail design.

FIG. 7*a* shows a view similar to FIG. 1, in which a first probe assembly 100*a* and a probe support 110*a* are designed to fit into a dovetail 13*a* of a first rotor disc 15*a*. Dovetail 13*a* is characterized by a dimension Da.

In FIG. 7*b*, a second probe assembly 100*b* and a probe support 110*b* fit into a dovetail 13*b* of a second rotor disc 15*b*. Dovetail 13*b* is characterized by a dimension Db, where dimension Db is different from dimension Da.

What is claim is:

1. An eddy current non-destructive inspection assembly configured for inspecting the internal test surface of a first group of cavities during a first inspection session and a second group of cavities during a second inspection session, wherein the cavities in the first group have substantially the same first set of size and shape, and the cavities in the second group have substantially the same second set of size and shape, and the first set and the second sets of size and shape are different, and each group of cavities has its respective axial direction and cross-section plane;

wherein the assembly comprises:

an eddy current array probe unit having a plurality of sensors;

a first probe support and a second probe support, onto which the probe unit is attached, the first probe support and the second probe support are configured to push the probe unit against the test surface of each of the first group of cavities or of the second group of cavities, respectively, and to be self-guiding to be snuggly fit within the respective cavities;

a manipulator configured to be attached exchangeably to the first or the second probe support via a manipulator link member and to drive the respective probe support into and out of the respective cavities only in the respective cavity axial direction, wherein each of the probe support is not confined by the manipulator in any other dimensions than the axial direction;

a driving handle to which the manipulator is attached to, configured to be used to drive the manipulator during the respective inspection sessions;

wherein the first or the second series of cavities each has two respective ending walls which are substantially perpendicular to the respective axial direction of the respective cavities, and wherein the manipulator further comprises:

a shaft transferring driving force from the driving handle along the axial direction, a shaft linear bearing keeping the shaft to move in the axial direction, and a swivel base having a least one pair of shoes, being pushed against one of the ending walls of one series of the cavities during one of the inspection sessions, wherein the linear bearing is affixed to the swivel base via a pivot so that when the swivel base is pushed snuggly against the one of the ending walls, there is a predetermined degree of freedom of movement between the shaft and the swivel base in a plane parallel to the axial direction and perpendicular to the ending walls, allowing a degree of tolerance in perpendicularity between a specific dovetail cavity and the ending walls.

2. The assembly of claim 1, wherein the first or the second probe support is built to fit for the first set or the second set of size and shape for the respective group of cavities, the probe support is partially rigid and slightly expandable in directions orthogonal to the respective test surface for self-guiding the probe support within the respective group of cavities and pushing the probe unit snuggly against the test surface.

3. The assembly of claim 2, wherein the first and the second groups of cavities are shaped in a first and second series of dovetails, and the tops of the first and the second probe supports are correspondingly Ω-shaped to be fit into and out of the respective cavities of the dovetails.

4. The assembly of claim 3, wherein the probe support is built of solid structure, and when looked in the cross-section direction, comprising at least a pair of symmetrically located slits within the structure effectuating a spring-loaded force in the lower part of the Ω-shape so that the probe support is slightly expandable in directions orthogonal to the test surface.

5. The assembly of claim 4, wherein the probe support, when looked in the cross-section direction, forming a pair of symmetrically located pivot points effectuating spring loaded force within the lower part of Ωshaped probe support such that the probe support pushes against the inside surface of the cavities through the entire length of the probe support in the axial direction.

6. The assembly of claim 4, wherein the size and shape of each set of the probe support is configured to have a tolerance of +/−0.05 mm from the corresponding dovetail.

7. The assembly of claim 1, wherein each of the linear bearing and the swivel base has its respective handle facilitating the adjustment of the freedom of movement.

8. The assembly of claim 1, wherein the manipulator link member has an elongated form including two ball-joints at its two ends, with one ball joint connecting the manipulator shaft and the other ball joint connecting the first probe support or the second probe support, exchangeably, wherein the link member allows free movement of the connecting probe support in all directions, except in the axial direction of the respective cavities that it serves to transfer the force from the driving handle to drive the probe support.

9. The assembly of claim 1, wherein the probe unit is attached onto the probe support using means so that the probe unit does not experience movement relative to the probe support and subsequently the locations of each of the plurality of sensors in the cross-section plane are known.

10. The assembly of claim 9, wherein the probe unit has a form of mat or sheet with flexible backing.

11. The assembly of claim 9, wherein the probe unit comprising groups of sensors, each group consisting of any number of sensors.

12. The assembly of claim 9, wherein the probe unit is attached to the probe support using re-attachable means.

13. The assembly of claim 12, wherein the re-attachable means including applying adhesive material between the probe unit and one of the probe supports.

14. The assembly of claim 9, wherein the probe unit is permanently attached to one of the probe supports.

15. The assembly of claim 9 further including an encoding unit configured to encode the position of the manipulator, by which the axial position of each of the plurality of sensors relative to each of the dovetail cavities during the first or second operation sessions is recorded.

16. The assembly of claim 1, wherein one of the first or the second probe support can be either pushed or pulled through any one of the corresponding cavities along the axial direction during one of the inspection sessions.

* * * * *